United States Patent
Kondo et al.

[11] Patent Number: 6,049,003
[45] Date of Patent: Apr. 11, 2000

[54] AZOAMIDINE COMPOUND

[75] Inventors: Suguru Kondo; Seiji Hirose; Kazuo Shiraiki, all of Saitama, Japan

[73] Assignee: Wako Pure Chemical Industries, Ltd., Osaka, Japan

[21] Appl. No.: 09/256,313

[22] Filed: Feb. 24, 1999

[30] Foreign Application Priority Data

Feb. 26, 1998 [JP] Japan ................................. 10-064270

[51] Int. Cl.⁷ ................................................ C07C 245/04
[52] U.S. Cl. ............................................ 562/440; 562/560
[58] Field of Search ..................... 562/440, 560

[56] References Cited

FOREIGN PATENT DOCUMENTS

| | | |
|---|---|---|
| 61-63643 | 4/1986 | Japan . |
| 63-310860 | 12/1988 | Japan . |
| 2-261 | 1/1990 | Japan . |

OTHER PUBLICATIONS

Patent Abstracts of Japan, vol. 013, No. 156 (C–585), Apr. 14, 1989 & JP 63 310860 A (Wako Pure Chem Ind Ltd), Dec. 19, 1988.

Patent Abstracts of Japan, vol. 014, No. 123 (C–0698), Mar. 8, 1990 & JP 02 000261 A (Wako Pur Chem Ind Ltd), Jan. 5, 1990.

Database CAPLUS on STN, Acc. No. 1989:497945, Miyagawa et al., 'Azoamidines and their salts for functional polymerization initiators.' JP 63310860 (abstract), 1989.

Primary Examiner—Gary Geist
Assistant Examiner—Brian J. Davis
Attorney, Agent, or Firm—Armstrong, Westerman, Hattori, McLeland and Naughton

[57] ABSTRACT

Azoamidine compounds shown by the general formula [1]

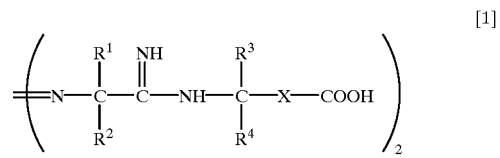

wherein $R^1$ and $R^2$ are independently a lower alkyl group, $R^3$ and $R^4$ are independently a hydrogen atom or a lower alkyl group, and X is a divalent hydrocarbon group, or its hydrate, show high reactivity and are capable of forming an intramolecule salt with an amidino group and having high solubility into water, methanol and other solvents.

8 Claims, No Drawings

AZOAMIDINE COMPOUND

BACKGROUND OF THE INVENTION

Azoamidine compounds have been useful as a polymerization initiator in polymerization of acrylamide, allylamine, vinyl pyrrolidone, etc., in production of cationic polymers and in various kinds of emulsion polymerizations.

However, those compounds have generally been used as their mineral acid salts such as hydrogen halide salts, and therefore they are accompanied with such defects that they may corrode manufacturing equipment in some cases and, in case where a polymer obtained by polymerization using those compounds as a polymerization initiator is used in cationic electrodeposition, rust-inhibiting effect of the dry paint film formed thereby may be reduced.

In order to dissolve those problems, some organic acid salts such as organic sulfonic acid salts of azoamidines have been evaluated (JP-A 2-261, etc.), but they have not yet been made into practical use because of their insufficient stability.

On the other hand, graft copolymers and block copolymers have been attracted as functional polymers which are expected to show various kinds of functions effectively, and there have actively been conducted such studies as synthesizing graft copolymers and block copolymers utilizing a terminal functional group of polymers obtained with the use of azo compounds having functional groups. Therefore, azo compounds having terminal functional groups have vigorously been required.

In compliance with this requirement, the present inventors have already developed azoamidine compounds wherein an α-amino acid residue is introduced as azoamidine compounds containing reactive functional groups and free from the problems of known azoamidine compounds which are caused by their form of mineral acid salts, and have filed patent applications (JP-A 63-310860) relating to those compounds.

However, all of the azoamidine compounds wherein an α-amino acid residue is introduced, which are disclosed in the above Patent Publication, are not enough in their solubility into water, methanol and other solvents and thus they have not yet been made into practical use. That is, there have not yet been found azoamidine compounds having such characteristics as having reactive functional groups at the terminal position, containing no halogen atoms and showing sufficient solubility into water, methanol, and other solvents as well, of which realization has recently been demanded.

SUMMARY OF THE INVENTION

The present invention has been conducted under the circumstances mentioned above and its object is to provide novel azoamidine compounds having terminal carboxylic groups which show high reactivity and are capable of forming an intramolecule salt with an amidino group and having high solubility into water, methanol and other solvents.

When those compounds are used as a polymerization initiator, corrosion of manufacturing equipment can be prevented, and in case where a polymer obtained by polymerization using the polymerization initiator is used in cationic electrodeposition, reduction of rust-inhibiting effect of the dry paint film formed thereby can be prevented. Moreover, those compounds make it possible to introduce effectively a high reactive carboxylic group into a terminal position of various kinds of polymers.

Further, those compounds are expected to show high emulsion stability in emulsion polymerization and to improve the stability of latex particle surface, because they contain no halogen atoms in the molecule.

The present invention relates to a compound shown by the general formula [1]

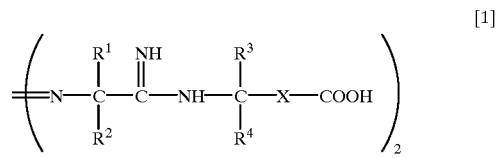

wherein $R^1$ and $R^2$ are independently a lower alkyl group, $R^3$ and $R^4$ are independently a hydrogen atom or a lower alkyl group, and X is a divalent hydrocarbon group, or its hydrate (hereinafter abbreviated as the azoamidine compound of the present invention).

Further, the present invention relates to a polymerization initiator, which comprises the above compound or its hydrate.

Still further, the present invention relates to a method for polymerization of α,β-ethylenically unsaturated monomer, which comprises the above compound or its hydrate as a polymerization initiator.

DETAILED DESCRIPTION OF THE PREFERRED EMBODIMENTS

For the purpose of attaining the above mentioned objects, the present inventors have earnestly investigated novel azoamidine compounds having terminal carboxylic groups which show high reactivity and are capable of forming an intramolecule salt with an amidine group, and having high solubility into water, methanol and other solvents.

The lower alkyl group shown by $R^1$, $R^2$, $R^3$ and $R^4$ in the general formula [1] may be straight chained, branched or cyclic and includes one having 1 to 5 carbon atoms, preferably 1 to 3 carbon atoms, which are specifically exemplified by a methyl group, an ethyl group, an n-propyl group, an isopropyl group, an n-butyl group, an isobutyl group, a tert-butyl group, a sec-butyl group, an n-pentyl group, an isopentyl group, a neopentyl group, a tert-pentyl group, a sec-pentyl group, a 2-methylbutyl group, a 1-ethylpropyl group, a 2-ethylpropyl group, a cyclopropyl group, a cyclobutyl group, a cyclopentyl group.

The divalent hydrocarbon group shown by X includes an alkylene group, an arylene group, an alkylene group containing an aromatic group, etc.

The alkylene group may be straight chained, branched or cyclic and one having 1 to 6 carbon atoms, preferably 1 to 4 carbon atoms. The specific examples of the alkylene group are straight chained alkylene groups such as a methylene group, an ethylene group, a trimethylene group, a tetramethylene group, a pentamethylene group and a hexamethylene group; branched alkylene groups such as a methylmethylene group, a propylene group, a 1,1-dimethylethylene group, a 1,2-dimethylethylene group, an ethylethylene group and a 2-methyltrimethylene group; cyclic alkylene groups such as a cyclopropylene group, a 1,3-cyclopentylene group and a 1,4-cyclohexylene group.

The arylene group may be monocyclic, condensed polycyclic or non-condensed polycyclic, and is specifically exemplified by an o-phenylene group, an m-phenylene group, a p-phenylene group, a 2,7-naphthylene group, a 1,1'-biphenyl-4,4'-diyl group, etc.

The alkylene group containing an aromatic group is one of which aromatic group may be placed at an intermediate position or a terminal position in the alkylene group, and is specifically exemplified by a phenylmethylene group, a phenylethylene group, —CH$_2$—C$_6$H$_4$—, —CH$_2$—C$_6$H$_4$—CH$_2$—, etc.

The specific examples of the azoamidine compound of the present invention shown by the above general formula [1] are as follows;

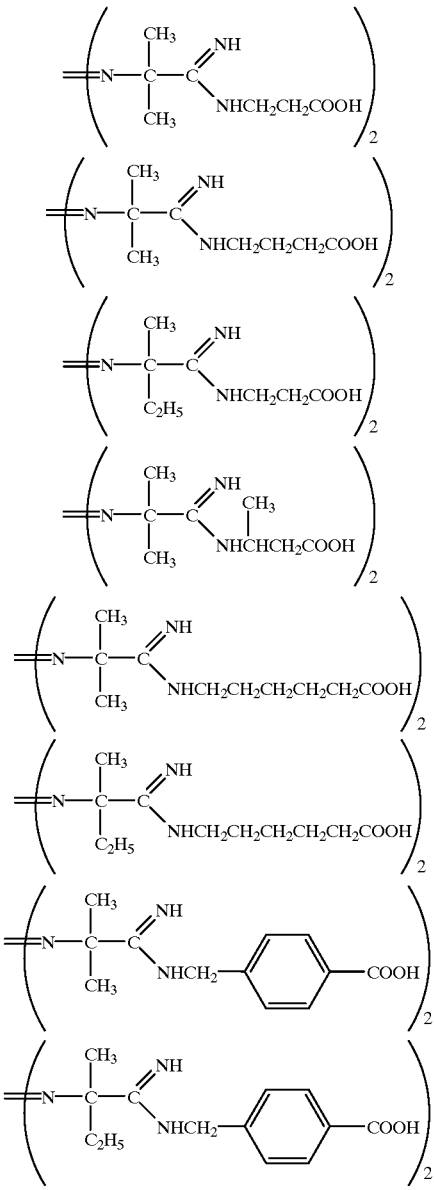

The azoamidine compound of the present invention can be obtained by reacting an azodiimino ether compound shown by the general formula [2]

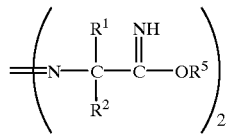

wherein R$^5$ is a lower alkyl group and R$^1$ and R$^2$ are as defined above, with an amino acid compound shown by the general formula [3]

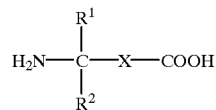

wherein R$^3$, R$^4$ and X are as defined above, in the absence or presence of a suitable solvent, whereby the object compound can easily be obtained.

The lower alkyl group shown by R$^5$ in the general formula [2] may be straight chained or branched and includes one having 1 to 6 carbon atoms, preferably 1 to 4 carbon atoms, which are specifically exemplified by a methyl group, an ethyl group, an n-propyl group, an isopropyl group, an n-butyl group, an isobutyl group, a tert-butyl group, a sec-butyl group, an n-pentyl group, an isopentyl group, a tert-pentyl group, a sec-pentyl group, a neopentyl group, an n-hexyl group, etc.

The specific examples of the azodiimino ether compound shown by the general formula [2] are 2,2'-azobis(1-imino-2-methylpropylmethyl ether), 2,2'-azobis(1-imino-2-methylpropylethyl ether), 2,2'-azobis(1-imino-2-methylpropyl-n-propyl ether), 2,2'-azobis(1-imino-2-methylpropylisopropyl ether), 2,2'-azobis(1-imino-2-methylpropyl-n-butyl ether), 2,2'-azobis(1-imino-2-ethylpropylmethyl ether), 2,2'-azobis(1-imino-2-ethylpropylethyl ether), etc.

The specific examples of the amino acid compound shown by the general formula [3] are β-alanine, β-aminobutyric acid, γ-aminobutyric acid, δ-amino-n-valeric acid, p-aminomethyl benzoic acid, etc.

The reaction solvent includes a hydrocarbon such as toluene, xylene, benzene, cyclohexane, n-hexane and n-octane, an alcohol such as methanol, ethanol, n-propanol, isopropanol, n-butanol, isobutanol, and tert-butanol, a halogenated hydrocarbon such as carbon tetrachloride, chloroform, methylene chloride, dichloroethane and trichloroethane, an ester such as ethyl acetate, butyl acetate and methyl propionate, dimethylformamide, dimethylsulfoxide, water, etc.

These solvents may be used alone or in a suitable combination of two or more thereof.

An amount of the amino acid compound to be used which is shown by the general formula [3] depends on the kind of amino acid compound and the azodiimino ether compound to be used, and it is generally 1.5 to 10 moles, preferably 2 to 5 moles per mole of the azodiimino ether compound.

A reaction temperature is not specifically limited, but when it is too high, azo groups are decomposed, and when it is too low, the reaction speed becomes low so that longer reaction time is required, and thus it is generally −10 to 40° C., preferably 0 to 30° C.

A reaction time depends on the kind of the azodiimino ether compound and the amino acid compound, and it is generally 1 to 24 hours.

Reaction operations and after-treatments other than the above may be conducted according to any of conventional ones in a similar kind of reaction.

As the azodiimino ether compound shown by the general formula [2] and the amino acid compound shown by the general formula [3] which are used in the production of the azoamidine compound of the present invention which is shown by the general formula [1], commercially available one may be used or one obtained by synthesizing after a convention manner may be used.

Thus obtained azoamidine compound of the present invention can easily give radicals as well as nitrogen gas by decomposition of the azo group on heating or irradiation of lights, and therefore when a various kind of polymerizable monomers coexists in the system, this monomer can rapidly be polymerized.

Polymerization or copolymerization of polymerizable monomers using the azoamidine compound of the present invention as a polymerization initiator can be realized by subjecting the azoamidine compound of the present invention and the polymerizable monomer to a polymerization reaction in the absence or presence of a suitable solvent, if necessary, under inert gas atmosphere, after a conventional manner.

The above polymerizable monomer includes α,β-ethylenically unsaturated monomer shown by the general formula [4]

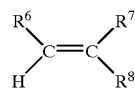

wherein $R^6$ is a hydrogen atom, a lower alkyl group, a carboxyl group, a carboxyalkyl group, an alkyloxycarbonyl group, a hydroxyalkyloxycarbonyl group, a cyano group or an aldehyde group, $R^7$ is a hydrogen atom, a lower alkyl group, a carboxyl group, an alkyloxycarbonyl group, a hydroxyalkyloxycarbonyl group, a cyano group or a halogen atom, $R^8$ is a hydrogen atom, a lower alkyl group, a haloalkyl group, a hydroxy group, an aryl group which may have a substituent, an aliphatic heterocyclic group, an aromatic heterocyclic group, a halogen atom, an alkyloxycarbonyl group, a hydroxyalkyloxycarbonyl group, a sulfonic acid group, a cyano group, a cyano-containing alkyl group, an acyloxy group, a carboxyl group, a carboxyalkyl group, an aldehyde group, an amino group, an aminoalkyl group, a carbamoyl group, an N-alkylcarbamoyl group or a hydroxyalkyl group, and $R^6$ and $R^7$ may combine with each other to form an aliphatic ring together with neighboring —C=C—.

The lower alkyl group shown by $R^6$ to $R^8$ in the general formula [4] may be straight chained, branched or cyclic and includes one having 1 to 6 carbon atoms, which are specifically exemplified by a methyl group, an ethyl group, an n-propyl group, an isopropyl group, an n-butyl group, an isobutyl group, a tert-butyl group, a sec-butyl group, a pentyl group, an isopentyl group, a tert-pentyl group, a 1-methylpentyl group, an n-hexyl group, an isohexyl group, a cyclopropyl group, a cyclopentyl group, a cyclohexyl group, etc.

The carboxyalkyl group shown by $R^6$ and $R^8$ includes the lower alkyl groups mentioned above whose hydrogen atom is substituted by a carboxyl group, and are specifically exemplified by a carboxymethyl group, a carboxyethyl group, a carboxyproryl group, a carboxybutyl group, a carboxypentyl group, a carboxyhexyl group, etc.

The alkyloxycarbonyl group shown by $R^6$ to $R^8$ includes preferably one having 2 to 11 carbon atoms, which are specifically exemplified by a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, a 2-ethylhexyloxycarbonyl group, an octyloxycarbonyl group, a nonyloxycarbonyl group, a decyloxycarbonyl group, etc.

The hydroxyalkyloxycarbonyl group shown by $R^6$ to $R^8$ includes the alkyloxycarbonyl group having 2 to 11 carbon atoms mentioned above whose hydrogen atom is substituted by a hydroxy group, and are specifically exemplified by a hydroxymethoxycarbonyl group, a hydroxyethoxycarbonyl group, a hydroxypropoxycarbonyl group, a hydroxybutoxycarbonyl group, a hydroxypentyloxycarbonyl group, a hydroxyhexyloxycarbonyl group, a hydroxyheptyloxycarbonyl group, a hydroxyoctyloxycarbonyl group, a hydroxynonyloxycarbonyl group, a hydroxydecyloxycarbonyl group, etc.

The halogen atom shown by $R^7$ and $R^8$ includes fluorine, chlorine, bromine and iodine.

The haloalkyl group shown by $R^8$ includes one obtained by halogenating (fluorinating, chlorinating, brominating, iodinating, etc.) the lower alkyl group having 1 to 6 mentioned above, and are specifically exemplified by a chloromethyl group, a bromomethyl group, a trifluoromethyl group, a 2-chloroethyl group, a 3-chloropropyl group, a 3-bromopropyl group, a 3,3,3-trifluoropropyl group, a 4-chlorobutyl group, a 5-chloropentyl group, 6-chlorohexyl group, etc.

The aryl group in the aryl group which may be substituted includes a phenyl group, a tolyl group, a xylyl group, a naphthyl group, etc., and the substituent includes an amino group, a hydroxy group, a lower alkoxy group, a carboxyl group, etc. and the substituted aryl group is specifically exemplified by an aminophenyl group, a toluidino group, a hydroxyphenyl group, a methoxyphenyl group, a tert-butoxyphenyl group, a carboxyphenyl group, etc.

The aliphatic heterocyclic group includes preferably 5- or 6-membered one containing 1 to 3 hetero atoms such as a nitrogen atom, an oxygen atom and a sulfur atom and is specifically exemplified by a pyrrolidyl-2-one group, a piperidyl group, a piperidino group, a piperazinyl group, a morpholino group, etc.

The aromatic heterocyclic group includes preferably 5- or 6-membered one containing 1 to 3 hetero atoms such as a nitrogen atom, an oxygen atom and a sulfur atom and is specifically exemplified by a pyridyl group, an imidazolyl group, a thiazolyl group, a furanyl group, a pyranyl group, etc.

The cyano-containing alkyl group includes the lower alkyl group mentioned above whose hydrogen atom is substituted by a cyano group and is specifically exemplified by a cyanomethyl group, a 2-cyanoethyl group, a 2-cyanopropyl group, a 3-cyanopropyl group, a 2-cyanobutyl group, a 4-cyanobutyl group, a 5-cyanopentyl group, a 6-cyanohexyl group, etc.

The acyloxy group includes one having 2 to 20 carbon atoms derived from a carboxylic acid and is specifically exemplified by an acetyloxy group, a propionyloxy group, a butyryloxy group, a pentanoyloxy group, a hexanoyloxy group, a heptanoyloxy group, an octanoyloxy group, a nonanoyloxy group, a decanoyloxy group, a benzoyloxy group, etc.

The aminoalkyl group includes the lower alkyl group mentioned above whose hydrogen atom is substituted by an amino group and is specifically exemplified by an aminomethyl group, an aminoethyl group, an aminopropyl group, an aminobutyl group, an aminopentyl group, an aminohexyl group, etc.

The N-alkylcarbamoyl group includes a carbamoyl group whose hydrogen atom is substituted by an alkyl group and is specifically exemplified by an N-methylcarbamoyl group, an N-ethylcarbamoyl group, an N-n-propylcarbamoyl group, an N-isopropylcarbamoyl group, an N-n-butylcarbamoyl group, an N-t-butylcarbamoyl group, etc.

The hydroxyalkyl group includes the lower alkyl group mentioned above whose hydrogen atom is substituted by a hydroxy group and is specifically exemplified by a hydroxymethyl group, a hydroxyethyl group, a hydroxypropyl group, a hydroxybutyl group, a hydroxypentyl group, a hydroxyhexyl group, etc.

The aliphatic ring formed by $R^6$, $R^7$ and —C=C—, includes an unsaturated aliphatic ring having 5 to 10 carbon atoms and the ring may be monocyclic or polycyclic, which is specifically exemplified by a norbornene ring, a cyclopentene ring, a cyclohexene ring, a cyclooctene ring, a cyclodecene ring, etc.

The specific examples of the α,β-ethylenically unsaturated monomer are ethylenically unsaturated aliphatic hydrocarbons having 2 to 20 carbon atoms such as ethylene, propylene, butylene and isobutylene; ethylenically unsaturated aromatic hydrocarbons having 8 to 20 carbon atoms such as styrene, 4-methylstyrene, 4-ethylstyrene and divinylbenzene; alkenyl esters having 3 to 20 carbon atoms such as vinyl formate, vinyl acetate, vinyl propionate and isopropenyl acetate; halogen-containing ethylenically unsaturated compounds having 2 to 20 carbon atoms such as vinyl chloride, vinylidene chloride, and vinylidene fluoride; ethylenically unsaturated carboxylic acids having 3 to 20 carbon atoms such as acrylic acid, methacrylic acid, itaconic acid, maleic acid, fumaric acid, crotonic acid, vinyl acetic acid, allyl acetic acid and vinyl benzoic acid (each of these acids may be in the form a salt such as an alkali metal salt (e.g. a sodium salt or a potassium salt), an ammonium salt or the like); ethylenically unsaturated carboxylic acid esters having 4 to 20 carbon atoms such as methyl methacrylate, ethyl methacrylate, propyl methacrylate, butyl methacrylate, 2-ethylhexyl methacrylate, stearyl methacrylate, methyl acrylate, ethyl acrylate, butyl acrylate, 2-ethylhexyl acrylate, lauryl methacrylate, stearyl acrylate, methyl itaconate, ethyl itaconate, methyl maleate, ethyl maleate, methyl fumarate, ethyl fumarate, methyl crotonate, ethyl crotonate and methyl 3-butenate; cyano-containing ethylenically unsaturated compounds having 3 to 20 carbon atoms such as acrylonitrile, methacrylonitrile and allyl cyanide; ethylenically unsaturated amide compounds having 3 to 20 carbon atoms such as acrylamide and methacrylamide; ethylenically unsaturated aldehydes having 3 to 20 carbon atoms such as acrolein and croton aldehyde; ethylenically unsaturated sulfonic acids having 2 to 20 carbon atoms such as vinyl sulfonic acid and 4-vinyl benzene sulfonic acid (each of these acids may be in the form a salt, for example, an alkali metal salt such as sodium and potassium salt); ethylenically unsaturated aliphatic amines having 2 to 20 carbon atoms such as vinylamine and allylamine; ethylenically unsaturated aromatic amines having 8 to 20 carbon atoms such as vinyl aniline; ethylenically unsaturated aliphatic heterocyclic amines having 5 to 20 carbon atoms such as N-vinyl pyrrolidone and vinyl piperidine; ethylenically unsaturated aromatic heterocyclic amines having 5 to 20 carbon atoms such as vinyl pyridine and 1-vinylimidazole; ethylenically unsaturated alcohols having 3 to 20 carbon atoms such as allyl alcohol and crotyl alcohol; ethylenically unsaturated phenols having 8 to 20 carbon atoms such as 4-vinylphenol, etc.

As a polymerization initiator in the polymerization reaction, use may be made of one or more of the azoamidine compound of the present invention or of a combination of one or more of the azoamidine compound of the present invention and one or more of polymerization initiator other than the azoamidine compound of the present invention.

The polymerization initiator other than the azoamidine compound of the present invention includes an azo compound such as azobisisobutyronitrile, 2,2'-azobis (2,4-dimethylvaleronitrile), 2,2'-azobis(2-amidinopropane) dihydrochloride [2,2'-azobis(2-ethylpropion-amidine) dihydrochloride], 2,2'-azobis[2-(2-imidazolin)-2-yl] propane, 2,2'-azobisisobutylamide dihydrate, dimethyl 2,2'-azobis(2-methylpropionate) and 4,4'-azobis(4-cyanovaleric acid), a peroxide compound such as benzoyl peroxide and di-tert-butyl peroxide, a photo polymerization initiator such as benzoin ethyl ether.

The polymerization method includes solution polymerization, bulk polymerization, suspension polymerization, emulsion polymerization, etc.

The solvent used in the solution polymerization includes an ether such as tetrahydrofuran, diethylether and dioxane, an alcohol such as methanol, ethanol and isopropanol, N,N-dimethylformamide, dimethylsulfoxide, water, etc. These solvents may be used alone or in a suitable combination of two or more thereof.

In the emulsion polymerization, a conventional surfactant may be used.

The polymerization reaction is preferably conducted under inert gas atmosphere, and the inert gas includes nitrogen gas, argon gas, etc.

An amount of the azoamidine compound of the present invention to be used in the above polymerization reaction depends on the kind of the polymerizable monomer to be used, and when the azoamidine compound of the present invention is used alone, the amount is 0.01 to 100 wt %, preferably 0.05 to 50 wt %, of the polymerizable monomer.

When the azoamidine compound of the present invention is co-used with other polymerization initiator, the ratio of the both compounds is suitably selected taking the kind of the polymerization initiator, the kind of the polymerizable monomer, the desired characteristics of the resulting polymer, etc. into consideration.

A concentration of the polymerizable monomer in the solvent on polymerization reaction depends on the kind of the polymerizable monomer, and it is generally 5 to 100 wt % (no solvent), preferably 10 to 60 wt %.

A polymerization temperature is not specifically limited, but when it is too low, polymerization slowly proceeds as a result of that little decomposition of azo groups is caused, and on the other hand, when it is too high, controlling of polymerization is difficult as a result of that too much decomposition of azo groups is caused, and it is generally 20 to 150° C., preferably 30 to 100° C.

A polymerization reaction time depends on reaction conditions such as a reaction temperature, the kinds of the polymerizable monomer and the azoamidine compound of the present invention and concentration of reactants, and it is generally 2 to 24 hours.

The azoamidine compound of the present invention shows higher solubility into water, methanol and other solvents as compared with known azoamidine compounds containing no halogen atom in which an α-amino acid residue is introduced, and therefore a polymerization rate in a solution polymerization, emulsion polymerization, etc. with the use of the azoamidine compound of the present invention is remarkably higher than the case of the azoamidine compounds in which an α-amino acid residue is introduced.

Further, the azoamidine compound of the present invention contains no halogen atom in the molecule, and therefore, in case where the compound is used as a polymerization initiator in emulsion polymerization, etc., there is observed no dead-end phenomenon, which is accompanied with a case of using the typical known azoamidine compound, 2,2'-azobis(2-methylpropionamidine) dihydrochloride, and also the polymerization rate is higher.

Still further, the azoamidine compound of the present invention shows the following characteristics.

(1) The azoamidine compound of the present invention is not a mineral acid salt and thus a manufacturing equipment (a polymerization reaction equipment), where the azoamidine compound of the present invention is used as a polymerization initiator, are not corroded.

(2) In case where a polymer obtained by polymerization using the azoamidine compound of the present invention as a polymerization initiator is used in cationic electrodeposition, reduction of rust-inhibiting effect is not worried about.

(3) By conducting polymerization reactions using the azoamidine compound of the present invention as a polymerization initiator, a high reactive carboxylic group can be introduced with efficiency into a terminal position of various kinds of polymers, and by utilizing the carboxylic group, various kinds of functions can be given to the polymers.

(4) The azoamidine compound of the present invention has high reactive carboxylic groups at its terminal position, and therefore the reaction of the carboxylic group with a compound containing a reactive functional group makes it possible to synthesize various kinds of block copolymers to be desired.

(5) The azoamidine compound of the present invention contains no halogen atoms, and therefore high stability of emulsion in emulsion polymerization, etc. can be attained.

In the following, the present invention is further explained referring to Examples, Reference Examples and Experiments, and the present invention is not limited thereto by any means.

EXAMPLE

Example 1

To 158 g of toluene solution containing 34.2 g of 2,2'-azobis(1-imino-2-methylpropylmethyl ether) were added 24.1 g of β-alanine and 40 ml of water followed by reaction at 25° C. for 6 hours. After standing overnight, the resulting crystal precipitated was recovered by filtration, washed and dried to give 40.9 g of 2,2'-azobis[N-(2-carboxyethyl)-2-methylpropionamidine] dihydrate.

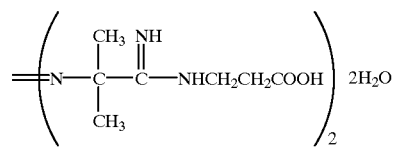

mp: 125.5° C. (dec.).

hu 1HNMR δ ppm ($D_2O$): 1.50 (12H, s, —$CH_3$), 2.57 (4H, t, —$C\underline{H}_2COOH$), 3.65 (4H, t, —$NHC\underline{H}_2$—).

UV: λ max371 nm ($E^{1\%}$=0.612/$CH_3OH$).

10 hours half life temperature =57° C.

Example 2

To 141 g of toluene solution containing 34.2 g of 2,2'-azobis(1-amino-2-methylpropylmethyl ether) were added 34 g of γ-amino-n-butyric acid and 40 ml of water followed by reaction at 25° C. to 30° C. for 6 hours. After standing overnight, the resulting crystal precipitated was recovered by filtration, washed and dried to give 37.0 g of 2,2'-azobis[N-(3-carboxypropyl)-2-methylpropionamidine].

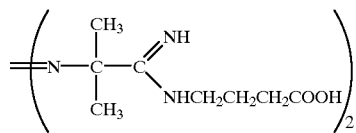

mp: 104° C. (dec.).

$^1$HNMR δ ppm ($D_2O$): 1.60 (12H, s, —$CH_3$), 1.95–2.05 (4H, m, —$CH_2C\underline{H}_2CH_2$—), 2.37 (4H, t, —$C\underline{H}_2COOH$), 3.52 (4H, t, —$NHC\underline{H}_2$—).

UV: λ max367 nm ($E^{1\%}$=0.631/$CH_3OH$).

Example 3

To 141 g of toluene solution containing 34.2 g of 2,2'-azobis(1-amino-2-methylpropylmethyl ether) were added 43.3 g of 6-amino-n-caproic acid and 40 ml of water followed by reaction at 25° C. to 30° C. for 6 hours. After standing overnight, the lower layer of the reaction solution was dropped into 1000 ml of acetone for crystallization, the resulting crystal was recovered by filtration, washed and dried to give 52.4 g of 2,2'-azobis[N-(5-carboxypentyl)-2-methylpropionamidine].

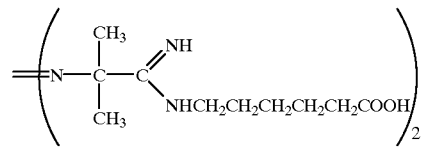

mp: 97° C. (dec.)

$^1$HNMR δ ppm ($D_2O$): 1.34–1.43 (4H, m, —$CH_2CH_2C\underline{H}_2CH_2CH_2$—), 1.53 (12H, s, —$CH_3$), 1.55–1.77 (8H, m, —$NHCH_2C\underline{H}_2CH_2C\underline{H}_2CH_2$—), 2.20 (4H, t, —$C\underline{H}_2COOH$), 3.45 (4H, t, —$NHC\underline{H}_2$—).

UV: λ max367 nm ($E^{1\%}$=0.600/$CH_3OH$).

Example 4

Acrylamide (20 g) was dissolved in 380 g of distilled water and 0.01 g of the azoamidine compound obtained in Example 1 was added thereto as a polymerization initiator. The reaction solution was heated at 50° C. with stirring under nitrogen gas atmosphere to cause polymerization reaction. After the polymerization reaction was started, samplings of the reaction solution were conducted at predetermined intervals, and the samples were precipitated by methanol to recover the produced polymer, followed by drying. The polymerization rates at each sampling time were measured.

The results together with decomposition rate constant at 50° C. are shown in Table 1.

Reference Examples 1 and 2

The same polymerization reaction as Example 4 was conducted except for using azoamidine compounds, in which an α-amino acid residue as introduced, of 2,2'-azobis (N-carboxymethyl-2-methylpropionamidine)

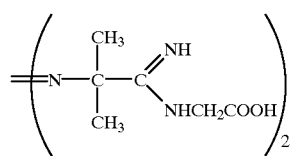

or 2,2'-azobis[N-(1-carboxyethyl)-2-methylpropionamidine]

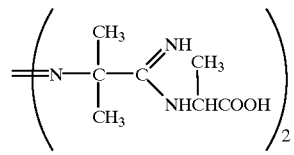

as a polymerization initiator.

The results together with decomposition rate constant at 50° C. are shown in Table 1.

compound, of 2,2'-azobis(2-methylpropionamidine) dihydrochloride as a polymerization initiator. The results are also shown in Table 2.

TABLE 2

Change of polymerization rate by polymerization time

| | Polymerization Rate(%) | | | | | | |
|---|---|---|---|---|---|---|---|
| Polymerization time | 1 H | 1.5 H | 2 H | 3 H | 4 H | 5 H | 6 H |
| Example 5 | 25.2 | 51.0 | 74.3 | 89.2 | 93.5 | 94.4 | 95.4 |
| Reference Example 3 | 32.0 | 37.1 | 69.9 | 88.4 | 91.4 | 93.1 | 92.2 |

As clear from Table 2, in case where an emulsion polymerization was conducted with the use of a typical known azoamidine compound, of 2,2'-azobis(2-methylpropionamidine)dihydrochloride as a polymerization initiator, a polymerization rate was reduced at 6 hour polymerization and later. That is, so-called dead end phenomenon was observed.

On the other hand, in case of using the azoamidine compound of the present invention as a polymerization initiator, no dead end phenomenon was observed and a polymerization rate was high.

TABLE 1

Change of polymerization rate by polymerization time

| | Polymerization Rate(%) | | | | | | Decomposition Rate Constant at 50° C. |
|---|---|---|---|---|---|---|---|---|
| Polymerization time | 1 H | 1.5 H | 2 H | 3 H | 4 H | 5 H | 6 H | (sec$^{-1}$) |
| Example 4 | 6.7 | 22.3 | 34.2 | 53.3 | 64.8 | 70.6 | 74.7 | 0.73 × 10$^{-5}$ |
| Reference Example 1 | 15.8 | 21.2 | 25.0 | 32.5 | 37.2 | 38.3 | 41.2 | 0.46 × 10$^{-5}$ |
| Reference Example 2 | 19.0 | 24.2 | 28.8 | 33.8 | 38.5 | 46.3 | 47.1 | 0.41 × 10$^{-5}$ |

As clear from Table 1, the polymerization rate is remarkably higher in case of conducting solution polymerization using the azoamidine compound of the present invention as a polymerization initiator as compared with a case of using azoamidine compounds in which an α-amino acid residue is introduced Example 5

Distilled water (400 g), sodium dodecyl sulfate (4 g) and azoamidine compound (0.5 g) obtained in Example 1 were mixed with one another and were stirred to give a solution, and 200 g of styrene monomer was added thereto, followed by stirring to make emulsion. The resultant was subjected to polymerization reaction at 50° C. with stirring under nitrogen gas atmosphere. After the polymerization reaction was started, samplings of the reaction solution were conducted at predetermined intervals, and the samples were precipitated by methanol to recover the produced polymer, followed by drying. The polymerization rates at each sampling time were measured.

The results are shown in Table 2.

Reference Example 3

The same emulsion polymerization as Example 5 was conducted except for using a typical known azoamidine Experiment 1

Solubility in various kinds of solvents were compared among the azoamidine compound of the present invention obtained in Example 1, and azoamidine compounds, in which an α-amino acid residue is introduced, of 2,2'-azobis(N-carboxymethyl-2-methylpropionamidine) used in Reference Example 1 and 2,2'-azobis[N-(1-carboxyethyl)-2-methylpropionamidine] used in Reference Example 2. The results are shown in Table 3.

TABLE 3

Comparison of solubility

| | Water | Methanol |
|---|---|---|
| Compound of Example 1 | 10.0% | 36.9% |
| Compound of Reference Example 1 | 0.4% | insoluble |
| Compound of Referenee Example 2 | 0.8% | insoluble |

As clear from Table 3, the azoamidine compound of the present invention has higher solubility to water and methanol as compared with azoamidine compounds in which an α-amino acid residue is introduced.

What is claimed is:

1. A compound shown by the general formula [1]

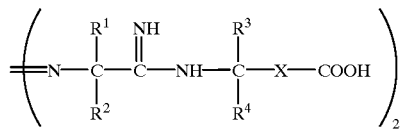

wherein $R^1$ and $R^2$ are independently a lower alkyl group, $R^3$ and $R^4$ are independently a hydrogen atom or a lower alkyl group, and X is a divalent hydrocarbon group, or its hydrate.

2. A compound according to claim 1, wherein both $R^3$ and $R^4$ are hydrogen atoms.

3. A compound according to claim 1, wherein a divalent hydrocarbon group shown by X is an alkylene group having 1 to 6 carbon atoms, an arylene group, or an alkylene group containing an aromatic group.

4. A compound according to claim 1, wherein a divalent hydrocarbon group shown by X is an alkylene group having 1 to 6 carbon atoms.

5. A compound according to claim 1, wherein both $R^1$ and $R^2$ are methyl groups, both $R^3$ and $R^4$ are hydrogen atoms and X is an alkylene group having 1 to 6 carbon atoms.

6. A compound according to claim 1, wherein both $R^1$ and $R^2$ are methyl groups, both $R^3$ and $R^4$ are hydrogen atoms and X is an alkylene group having 1 to 4 carbon atoms.

7. A polymerization initiator, which comprises the compound or its hydrate according to any one of claim 1 to 6.

8. A method for polymerization of $\alpha,\beta$-ethylenically unsaturated monomer, which comprises using the compound or its hydrate according to any one of claim 1 to 6 as a polymerization initiator.

* * * * *

UNITED STATES PATENT AND TRADEMARK OFFICE
CERTIFICATE OF CORRECTION

PATENT NO.   : 6,049,003
DATED        : April 11, 2000
INVENTOR(S)  : Kondo et al.

It is certified that error appears in the above-identified patent and that said Letters Patent is hereby corrected as shown below:

Title Page:
Item [75] Inventor change the third inventors name, "Kazuo SHIRAIKI" to be --Kazuo SHIRAKI--.

Signed and Sealed this

Third Day of July, 2001

Attest:

*Attesting Officer*

NICHOLAS P. GODICI
*Acting Director of the United States Patent and Trademark Office*